United States Patent [19]
Stalcup et al.

[11] Patent Number: 5,755,806
[45] Date of Patent: May 26, 1998

[54] METHOD OF ATTACHING SPIKES TO AN ORTHOPAEDIC IMPLANT

[75] Inventors: Gregory C. Stalcup, Columbia City; Clarence M. Panchison, Warsaw; Jack D. Jennings, Syracuse; Tracy R. Gilliland, Pierceton, all of Ind.

[73] Assignee: Bristol-Myers Squibb Co., New York, N.Y.

[21] Appl. No.: 724,556

[22] Filed: Sep. 30, 1996

[51] Int. Cl.$^6$ ........................................... A61F 2/32
[52] U.S. Cl. ................... 623/22; 623/18; 623/901; 228/135
[58] Field of Search .................. 623/901, 16, 18, 623/22, 23, 66; 29/525; 228/135, 139, 148, 171, 174, 262.71

[56] References Cited

U.S. PATENT DOCUMENTS

| | | | |
|---|---|---|---|
| 2,910,978 | 11/1959 | Urist | 128/92 |
| 3,528,109 | 9/1970 | Scales | 3/1 |
| 3,641,590 | 2/1972 | Michele | 3/1 |
| 3,683,421 | 8/1972 | Martinie | 3/1 |
| 3,685,058 | 8/1972 | Tronzo | 3/1 |
| 3,808,606 | 5/1974 | Tronzo | 3/1 |
| 3,840,904 | 10/1974 | Tronzo | 3/1 |
| 4,385,405 | 5/1983 | Teinturier | 3/1.912 |
| 4,563,778 | 1/1986 | Roche et al. | 623/16 |
| 4,566,138 | 1/1986 | Lewis et al. | 623/22 |
| 4,659,331 | 4/1987 | Matthews et al. | 623/20 |
| 4,769,041 | 9/1988 | Morscher | 623/22 |
| 4,778,473 | 10/1988 | Matthews et al. | 623/20 |
| 4,923,473 | 5/1990 | Griss et al. | 623/22 |
| 5,032,134 | 7/1991 | Lindwer | 623/23 |
| 5,116,339 | 5/1992 | Glock | 606/91 |
| 5,156,625 | 10/1992 | Marchetti et al. | 623/22 |
| 5,163,961 | 11/1992 | Harwin | 623/23 |
| 5,211,665 | 5/1993 | Ku | 623/22 |
| 5,255,838 | 10/1993 | Gladdish, Jr. et al. | 228/135 |
| 5,310,408 | 5/1994 | Schryver et al. | 623/22 |
| 5,314,492 | 5/1994 | Hamilton et al. | 623/16 |
| 5,314,494 | 5/1994 | Huiskes et al. | 623/23 |
| 5,326,368 | 7/1994 | Collazo | 623/22 |
| 5,360,452 | 11/1994 | Engelhardt et al. | 623/23 |
| B1 4,743,262 | 5/1994 | Tronzo | 623/22 |

FOREIGN PATENT DOCUMENTS

| | | |
|---|---|---|
| 0 169 978B1 | 2/1986 | European Pat. Off. |
| 44 35 497 C1 | 7/1996 | Germany. |
| 2 248 395 | 4/1992 | United Kingdom. |
| WO 85/02535 | 6/1985 | WIPO. |

OTHER PUBLICATIONS

Mallory Head Hip Program—Results That Can't Be Ignored—Biomet, Inc.—JBJS, Aug.1993.
PSL Total Hip Replacement System—Surgical Procedure—BioPro—No date available.
Discover—Duraloc Acetabular Cup System—Surgical Technique—DePuy—1990.
Addressing the Acetabular Crisis—Depuy—1990.
S-ROM® System—Cemented or Cementless Stem Designs—Joint Medical Products—1990.
Whiteside Total Hip System—Dow Corning Wright—1985.
BIAS™ Hip Prosthesis—Zimmer, Inc.—Literature No. 97–6550–01 (Rev. 3)—c1985,1988.
BIAS™ Total Hip System—Zimmer, Inc.—1985.

*Primary Examiner*—Michael J. Milano
*Assistant Examiner*—Tram Anh T. Nguyen
*Attorney, Agent, or Firm*—Margaret L. Geringer

[57] ABSTRACT

The invention is directed to a method of attaching spikes (34) to an orthopaedic implant such as an acetabular cup (22). The acetabular cup (22) is formed with at least one tapered hole (28) therein which extends from an outside diameter (30) to an inside diameter (32) of the cup. At least one spike (34) having a tapered end (38) is pressed into a corresponding tapered hole (28) of the cup (22), whereby an interference fit is created between the tapered end (38) and the tapered hole (28). The spike (34) is metallurgically bonded to the cup (22), such as by electron beam welding and heat treating. The inside diameter (32) of cup (22) is then finished.

29 Claims, 2 Drawing Sheets

METHOD OF ATTACHING SPIKES TO AN ORTHOPAEDIC IMPLANT

BACKGROUND OF THE INVENTION

1. Field of the Invention

The present invention relates to orthopaedic implants, and, more particularly, relates to orthopaedic implants having spikes extending therefrom, such as spiked acetabular cups.

2. Description of the Related Art

It is known to provide an acetabular cup with a plurality of spikes which extend from the outside diameter thereof. The spikes are received within the prepared pelvis, and assist in anchoring the acetabular cup to the pelvis. For example, it is known to drill a hole partially through an acetabular cup from the outside diameter of the cup. A spike is inserted within the hole, laser welded, and a beaded surface is then sintered over the outside diameter of the cup and around the perimeter of the spike. The laser welded and sintered bond between the spike and each of the cup and the beaded surface may act as the only interconnection between the cup and the spike. The spike may therefore become dislodged from the hole depending upon the strength of the bond between the spike and the cup and beaded surface.

It is also known to provide an acetabular cup having a plurality of spikes which are cast into or otherwise directly formed with the cup. In the event that a porous surface, such as a fiber metal surface, is to be fastened to the outside diameter of the cup, the spikes may interfere with the placement of the fiber metal pad and attachment between the fiber metal pad and the cup.

What is needed in the art is a method of relatively easily attaching a plurality of spikes to an implant, such as to the outside diameter of an acetabular cup, with an improved physical attachment between the spikes and the implant.

SUMMARY OF THE INVENTION

The present invention provides an orthopaedic implant assembly in which tapered spikes are press fit into corresponding holes in an orthopaedic implant, welded at the side of the implant opposite the extending spikes, heat treated with the implant, and machined off at the side of the implant opposite the extending spikes. The spikes extend from the bone contacting surface of the implant.

The invention comprises, in one form thereof, a method of attaching spikes to an acetabular cup. While the invention will be described with reference to an acetabular cup, it is understood that it is not limited thereto, but may be utilized on any suitable spiked implant. The acetabular cup is formed with at least one tapered hole therein which extends from an outside diameter to an inside diameter of the cup. At least one spike having a tapered end is pressed into a corresponding tapered hole of the cup, whereby an interference fit is created between the tapered end and the tapered hole. The spike is metallurgically bonded to the cup, such as by electron beam welding and heat treating, and then the inside diameter of the cup is machined or otherwise finished.

An advantage of the present invention is that the physical attachment between the implant and the spikes is improved.

Another advantage is that visible weld lines between the implant and the spikes are substantially reduced.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrate one preferred embodiment of the invention, in one form, and such exemplification is not to be construed as limiting the scope of the invention in any manner.

DETAILED DESCRIPTION OF THE INVENTION

Figure 1:
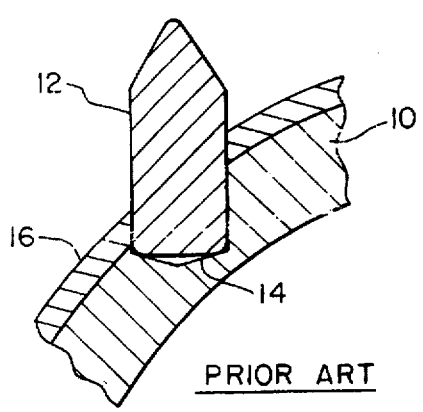
FIG. 1 is a fragmentary, sectional view of a conventional acetabular cup having a spike extending therefrom.

Referring now to the drawings, and more particularly to FIG. 1, there is shown a fragmentary, sectional view of a conventional acetabular cup 10 having a spike 12 extending therefrom. A hole 14 is drilled partially through cup 10 and opens at the outside diameter of cup 10. Cylindrical spike 12 is inserted within cylindrical hole 14, laser welded, and a beaded surface 16 is then sintered over the outside diameter of cup 10 and the perimeter of spike 12. The laser welded and sintered bond between spike 12 and each of cup 10 and beaded surface 16 may act as the only interconnection between cup 10 and spike 12. Spike 12 may therefore become dislodged from hole 14 depending upon the strength of the bond between spike 12 and the cup 10 and beaded surface 16.

Figure 2:
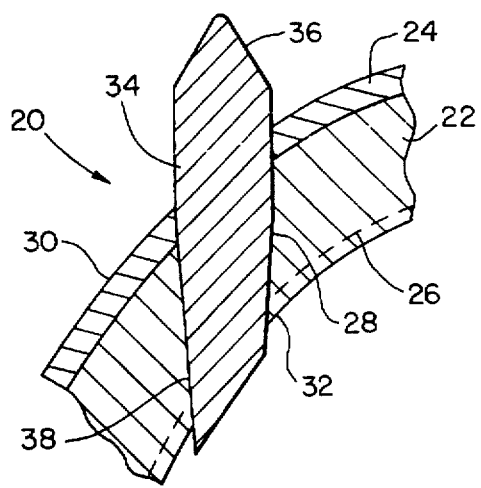
FIG. 2 is a fragmentary, sectional view of an embodiment of an acetabular cup assembly of the present invention with which the method of the present invention may be carried out, showing a tapered spike pressed into a hole in the acetabular cup.
Figure 3:
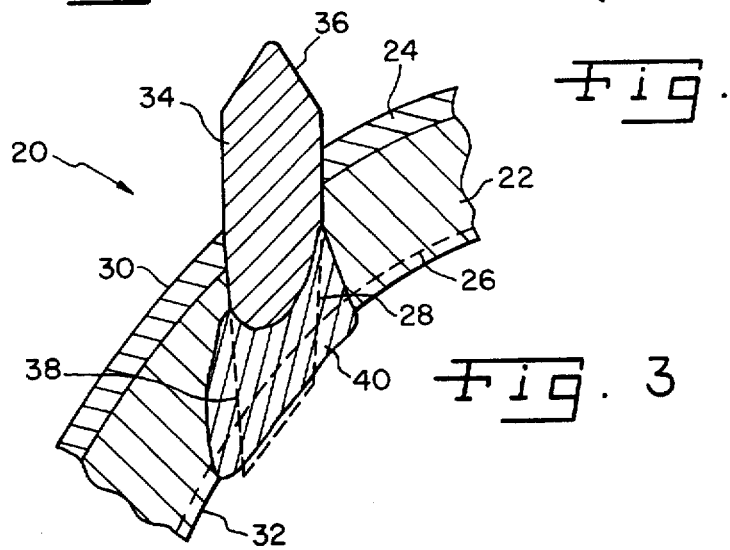
FIG. 3 is a fragmentary, sectional view of the acetabular cup assembly shown in FIG. 2, after the spike has been welded to the cup.
Figure 4:
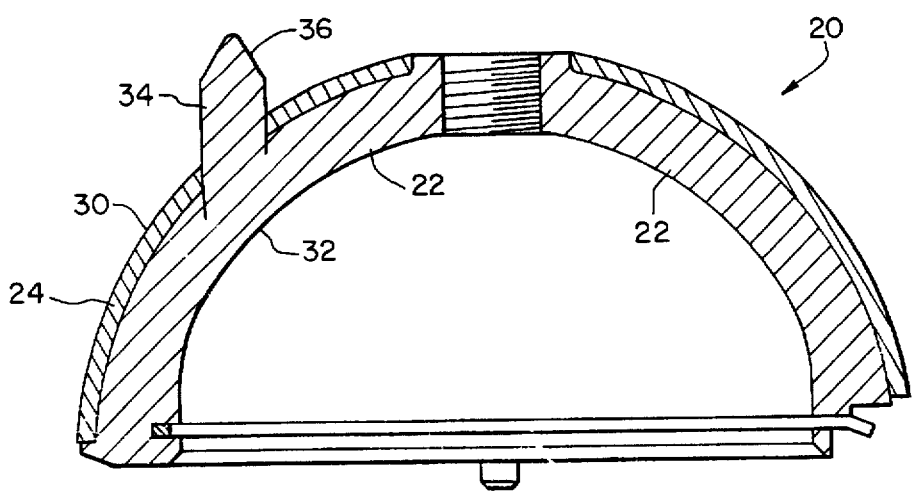
FIG. 4 is a sectional view of the acetabular cup assembly shown in FIGS. 2 and 3, after the inside diameter has been finished.

Referring now to FIGS. 2–4, there is shown an embodiment of an orthopaedic implant or acetabular cup assembly 20 of the present invention during the consecutive manufacturing steps associated therewith. Referring first to FIG. 2, an acetabular cup 22 is formed with a porous surface 24, such as a beaded surface or fiber metal surface, at the outside diameter thereof. A dashed line 26, disposed substantially parallel to the inside diameter of cup 22 represents the amount of material that is removed from the inside diameter of cup 22 during the manufacture of acetabular cup assembly 20, as will be described hereinafter. Cup 22 is formed with at least one tapered hole 28 extending from an outside diameter 30 to an inside diameter 32 thereof. Hole 28 is larger at outside diameter 30 and smaller at inside diameter 32 of cup 22.

At least one spike 34 is configured to be received within a respective hole 28 in cup 22. Each spike 34 includes a tip 36 which is adapted to be embedded within a bone which is shaped to receive acetabular cup assembly 20. Each spike 34 also includes a tapered end 38 which is sized and configured to be received within a respective hole 28 in cup 22. More particularly, tapered end 38 has a complimentary shape which is approximately the same as that of a corresponding tapered hole 28.

During manufacture, porous surface 24, such as fiber metal, is attached to the outside diameter of cup 22, such as by diffusion bonding. Thereafter, tapered hole 28 is formed through each of porous surface 24 and cup 22. Spike 34 is then pressed into a corresponding tapered hole 28, whereby an interference fit is created between tapered end 38 of spike 34 and tapered hole 28 of cup 22. A sufficient load is applied in order to provide a tight press fit. Such a press fit ensures that an intimate contact is created between spike 34 and cup 22. The press fit may tend to remove some surface irregularities at the outside diameter of spike 34 and the inside diameter of hole 28, and thereby create the interference fit with reduced interstitial spaces. The spike 34 may extend slightly beyond the inside diameter 32 at this stage, as shown in FIG. 2.

Referring now to FIG. 3, a fragmentary, sectional view of acetabular cup assembly 20 is shown after spike 34 is metallurgically bonded to cup 22. More particularly, the portion of tapered end 38 of spike 34 which extends from the inside diameter 32 of cup 22 is electron beam welded at inside diameter 32, as shown by a weld zone 40. The electron beam weld is preferably such that weld zone 40 has a penetration depth into cup 22 which extends beyond the portion to be removed at inside diameter 32 (illustrated by dashed line 26). In the particular embodiment shown in FIG. 3, the thickness of the portion to be removed at inside diameter 32 is approximately 0.050 inch and weld zone 40 has a penetration depth of greater than 0.050 inch. This assures that after the inside diameter 32 of cup 22 is finished (as will be described below), a weld zone still exists between spike 34 and cup 22.

After spike 34 is welded to cup 22, acetabular cup assembly 20 is heat treated to acquire desired metallic physical properties within cup 22. To wit, acetabular cup assembly 20 may be placed within a furnace and the temperature thereof increased to a temperature above a transient temperature of each of cup 22 and spike 34, and for a sufficient time, thereby resulting in the formation of new grain growth in weld zone 40 at the interface with each of cup 22 and spike 34. This improves the strength at the weld zone. For example, a temperature of about 1875° F. for about 4 hours has been found to be a sufficient time and temperature to produce new grain growth for a titanium alloy metal cup and spike.

Referring now to FIG. 4, a sectional view of acetabular cup assembly 20 is shown after inside diameter 32 is finished. More particularly, inside diameter 32 may be finished by removing approximately 0.050 inch of material therefrom using a turning process, such as with a lathe. The amount of material which is removed during the finishing process is sufficient to remove a portion of a weld zone 40 associated with each spike 34, and also to effect a desired surface finish and dimension at inside diameter 32. However, it is noted that subsequent to the heat treatment step, the actual weld zone area is no longer noticeable due to the new grain growth.

Figure 5:
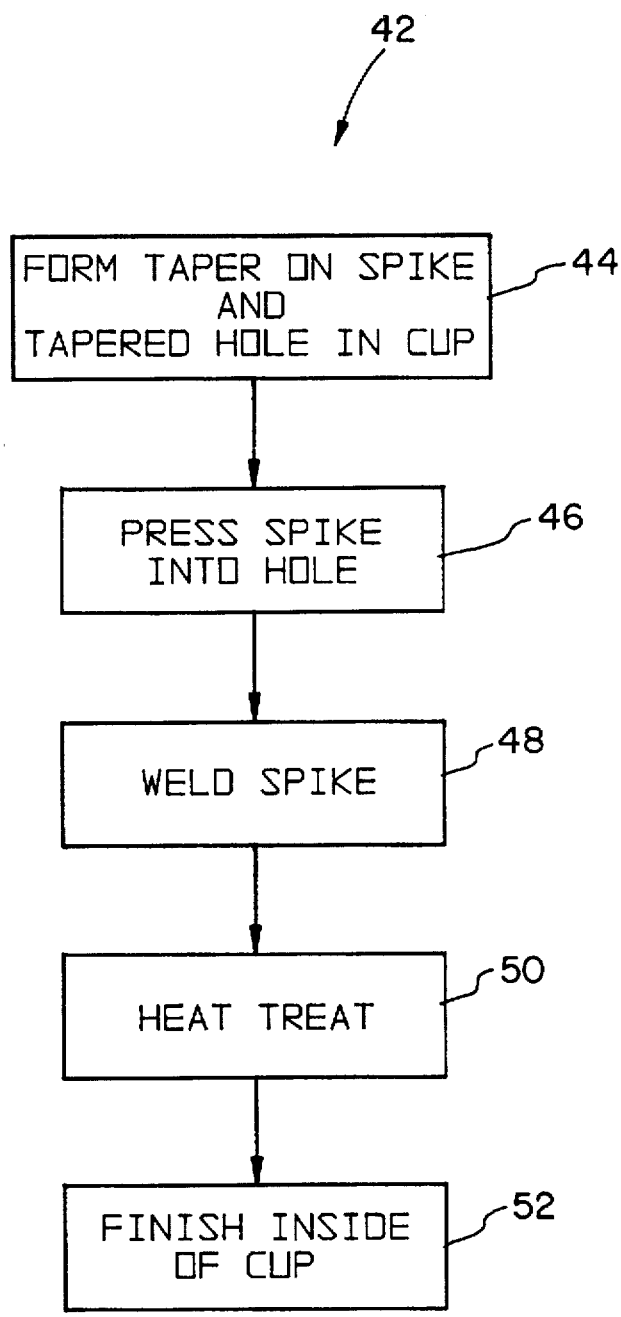
FIG. 5 is a flow chart illustrating an embodiment of the method of the present invention with reference to the acetabular cup assembly shown in FIGS. 2–4.

FIG. 5 illustrates an embodiment of a flowchart 42 for carrying out the method of the present invention. Flowchart 42 corresponds to the manufacture of acetabular cup assembly 20 shown in FIGS. 2–4, as described above. At block 44, a taper 38 is formed on each spike 34 which is to be connected with acetabular cup 20, and a corresponding number of tapered holes 28 are formed in cup 20. Each spike 34 is pressed into a corresponding hole 28 (block 46), as shown in FIG. 2. Thereafter, each spike 34 is metallurgically bonded to cup 22 by electron beam welding each spike 34 to cup 22 (block 48), as shown in FIG. 3. Acetabular cup assembly 20 is then heat treated to generate new grain growth at the interface between weld zone 40, cup 22 and spike 34 (block 50). The inside diameter of cup 22 is then finished using, e.g., a lathe process, to remove the portion of weld zone 40 from inside diameter 32 and effect a desired surface finish and dimension at inside diameter 32 (block 52 and FIG. 4).

In the embodiment of acetabular cup assembly shown in the drawings, spike 34 is formed with a tapered end 38 and cup 22 is formed with a tapered hole 28. However, it may also be desirable for a particular application to form each of spike 34 and cup 22 without tapered shapes (not shown). Configured as such, each spike 34 is formed with an outside diameter which is slightly larger than the inside diameter of a corresponding hole 28 such that an interference fit therebetween results when a spike 34 is pressed into a corresponding hole 28.

The cup 22 and spike 34 may be made of any suitable metal, such as a titanium alloy, although any suitable material may be utilized. In addition, the cup 22 of FIG. 4 may include a bearing surface (not shown) disposed on the inside diameter of the cup 22, as is known in the art. Such bearing surface may be made of ultra high molecular weight polyethylene, although any suitable material may be utilized.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of attaching metal spikes to a metal acetabular cup, comprising the steps of:

forming the metal acetabular cup having an outside diameter and an inside diameter with at least one tapered through hole therein, said hole extending from the outside diameter to the inside diameter of said metal cup;

forming at least one metal spike with a tapered end;

pressing each said spike into a corresponding said tapered hole of said cup, whereby an interference fit is created between said tapered end and said tapered hole; and metallurgically bonding each said spike to said cup.

2. The method of claim 1, comprising the further step of finishing said inside diameter of said cup subsequent to the metallurgically bonding step.

3. The method of claim 2, wherein said finishing step comprises removing approximately 0.050 inch of material from said inside diameter.

4. The method of claim 1, wherein said metallurgically bonding step comprises the sub-steps of:

welding each said spike to said cup; and heat treating said cup and said spikes.

5. A method of attaching spikes to an acetabular cup, comprising the steps of:

forming an acetabular cup with at least one tapered hole therein, said hole extending from an outside diameter to an inside diameter of said cup;

forming at least one spike with a tapered end;

pressing each said spike into a corresponding said tapered hole of said cup, whereby an interference fit is created between said tapered end and said tapered hole; and metallurgically bonding each said spike to said cup, wherein said metallurgically bonding step comprises the sub steps of:

welding each said spike to said cup; and heat treating said cup and said spikes, wherein said welding step comprises welding each said spike to said cup at said inside diameter of said cup.

6. A method of attaching spikes to an acetabular cup, comprising the steps of:

forming an acetabular cup with at least one tapered hole therein, said hole extending from an outside diameter to an inside diameter of said cup;

forming at least one spike with a tapered end;

pressing each said spike into a corresponding said tapered hole of said cup, whereby an interference fit is created between said tapered end and said tapered hole; and metallurgically bonding each said spike to said cup, wherein said metallurgically bonding step comprises the sub-steps of:

welding each said spike to said cup; and heat treating said cup and said spikes, wherein said welding step comprises welding each said spike to said cup with a penetration depth of at least 0.050 inch.

7. The method of claim 6, comprising the further step of finishing said inside diameter of said cup by removing about 0.050 inch of material from said inside diameter.

8. A method of attaching spikes to an acetabular cup, comprising the steps of:

forming an acetabular cup with at least one tapered hole therein, said hole extending from an outside diameter to an inside diameter of said cup;

forming at least one spike with a tapered end;

pressing each said spike into a corresponding said tapered hole of said cup, whereby an interference fit is created between said tapered end and said tapered hole; and metallurgically bonding each said spike to said cup, wherein said metallurgically bonding step comprises the sub-steps of:

welding each said spike to said cup; and heat treating said cup and said spikes, wherein said heat treating step comprises increasing a temperature of said cup and said spikes to a temperature above a transient temperature of said cup and said spikes.

9. A method of attaching spikes to an acetabular cup, comprising the steps of:

forming an acetabular cup with at least one tapered hole therein, said hole extending from an outside diameter to an inside diameter of said cup;

forming at least one spike with a tapered end;

pressing each said spike into a corresponding said tapered hole of said cup, whereby an interference fit is created between said tapered end and said tapered hole; and metallurgically bonding each said spike to said cup, wherein said metallurgically bonding step comprises the sub-steps of:

welding each said spike to said cup; and heat treating said cup and said spikes, wherein said welding step comprises electron beam welding each said spike to said cup.

10. A method of attaching metal spikes to a metal acetabular cup, comprising the steps of:

forming the metal acetabular cup having an outside diameter and an inside diameter with at least one through hole therein, said hole extending from the outside diameter to the inside diameter of said metal cup;

forming at least one metal spike;

pressing each said spike into a corresponding said hole of said cup, whereby an interference fit is created between said spike and said hole; and metallurgically bonding each said spike to said cup.

11. The method of claim 10, wherein said hole is formed as a tapered hole and each said spike is formed as a tapered spike.

12. The method of claim 10, comprising the further step of finishing said inside diameter of said cup subsequent to the metallurgically bonding step.

13. The method of claim 12, wherein said finishing step comprises removing about 0.050 inch of material from said inside diameter.

14. A method of attaching spikes to an acetabular cup, comprising the steps of:

forming an acetabular cup with at least one hole therein, said hole extending from an outside diameter to an inside diameter of said cup;

forming at least one spike;

pressing each said spike into a corresponding said hole of said cup, whereby an interference fit is created between said spike and said hole; and metallurgically bonding each said spike to said cup, wherein said metallurgically bonding step comprises the sub-steps of:

welding each said spike to said cup; and heat treating said cup and said spikes.

15. The method of claim 14, wherein said welding step comprises welding each said spike to said cup at said inside diameter of said cup.

16. The method of claim 14, wherein said welding step comprises welding each said spike to said cup with a penetration depth of at least 0.050 inch.

17. The method of claim 16, comprising the further step of finishing said inside diameter of said cup by removing about 0.050 inch of material from said inside diameter.

18. The method of claim 14, wherein said heat treating step comprises raising a temperature of said cup and said spikes to a temperature above a transient temperature of said cup and said spikes.

19. The method of claim 14, wherein said welding step comprises electron beam welding each said spike to said cup.

20. A method of attaching at least one metal spike to a metal orthopaedic implant, comprising the steps of:

forming the metal orthopaedic implant having a first side and second side with at least one through hole therein, said hole extending from the first side to the second side of the metal orthopaedic implant;

forming at least one metal spike which is used to affix the orthopaedic implant to a bone;

pressing each said spike into a corresponding said hole of said implant, whereby an interference fit is created between said spike and said hole; and metallurgically bonding each said spike to said implant.

21. The method of claim 20, wherein each said hole is formed as a tapered hole and each said spike is formed as a tapered spike.

22. The method of claim 20, wherein said metallurgically bonding step comprises the sub-steps of:

welding each said spike to said implant; and heat treating said implant and said spikes.

23. A method of attaching at least one spike to an orthopaedic implant, comprising the steps of:

forming an orthopaedic implant with at least one hole therein:

forming at least one spike which is used to affix the orthopaedic implant to a bone;

pressing each said spike into a corresponding said hole of said implant, whereby an interference fit is created between said spike and said hole; and metallurgically bonding each said spike to said implant, wherein said metallurgically bonding step comprises the sub-steps of:

welding each said spike to said implant; and heat treating said implant and said spikes, wherein said heat treating step comprises raising a temperature of said implant and said spikes to a temperature above a transient temperature of said implant and said spikes.

24. A method of attaching at least one spike to an orthopaedic implant comprising the steps of:

forming an orthopaedic implant with at least one hole therein;

forming at least one spike which is used to affix the orthopaedic implant to a bone;

pressing each said spike into a corresponding said hole of said implant, whereby an interference fit is created between said spike and said hole; and metallurgically bonding each said spike to said implant, wherein the metallurgically bonding step comprises bonding each said spike at a first side of the implant, and wherein the method further comprises the step of finishing the first side of the implant, said first side of the implant being oppositely located to a second side of the implant from which each said spike extends.

25. The method of claim 24, wherein said finishing step comprises removing material from said first side of the implant.

26. The method of claim 25, wherein said metallurgically bonding step comprises the sub-steps of:

welding each said spike to said implant; and heat treating said implant and said spikes.

27. The method of claim 26, wherein said welding step comprises welding each said spike to said implant with a penetration depth greater than the amount of material to be removed in the finishing step.

28. The method of claim 26, wherein said heat treating step comprises increasing a temperature of said implant and said spikes to a temperature above a transient temperature of said implant and said spikes for a sufficient time in order to produce new grain growth.

29. The method of claim 26, wherein said welding step comprises electron beam welding each said spike to said implant.

* * * * *